(12) United States Patent
Van Vyve (10) Patent No.: US 9,228,963 B2
(45) Date of Patent: Jan. 5, 2016

(54) STEAM QUALITY MEASUREMENT SYSTEM (75) Inventor: Albert R. L. M. Van Vyve, Chaudfontaine (BE)

(73) Assignee: Armstrong Global Holdings, Inc., Stuart, FL (US)

( * ) Notice: Subject to any disclaimer, the term of this patent is extended or adjusted under 35 U.S.C. 154(b) by 0 days.

(21) Appl. No.: 14/354,602

(22) PCT Filed: Aug. 31, 2012

(86) PCT No.: PCT/US2012/053353
§ 371 (c)(1),
(2), (4) Date: Apr. 28, 2014

(87) PCT Pub. No.: WO2013/062673
PCT Pub. Date: May 2, 2013

(65) Prior Publication Data
US 2014/0250979 A1    Sep. 11, 2014

Related U.S. Application Data

(60) Provisional application No. 61/552,557, filed on Oct. 28, 2011.

(51) Int. Cl.
*G01N 25/56* (2006.01)
*G01N 25/60* (2006.01)
*F22B 37/38* (2006.01)
*G01N 7/14* (2006.01)

(52) U.S. Cl.
CPC ............. *G01N 25/56* (2013.01); *F22B 37/38* (2013.01); *G01N 25/60* (2013.01); *G01N 7/14* (2013.01)

(58) Field of Classification Search
CPC ..................................................... G01N 25/56
See application file for complete search history.

(56) References Cited

U.S. PATENT DOCUMENTS

| 4,149,557 A | 4/1979 | Keech et al. |
| 4,561,785 A | 12/1985 | Long et al. |
| 4,833,688 A * | 5/1989 | Smith .............................. 374/42 |

FOREIGN PATENT DOCUMENTS

EP    1715302 A1    10/2006

OTHER PUBLICATIONS

International Preliminary Report on Patentability dated May 8, 2014 for International Application No. PCT/US2012/053353.
(Continued)

*Primary Examiner* — Laura Martin
*Assistant Examiner* — Alex Devito
(74) *Attorney, Agent, or Firm* — Brooks Kushman P.C.

(57) ABSTRACT

A system and method for continually and automatically measuring the quality of steam includes a steam dryness/superheat meter and a non-condensable gases (NCG) meter. The steam dryness meter includes a throttling calorimeter through which a steam sample enters at atmospheric pressure, sensors for sensing the pressure and temperature of the stream before and after it enters the calorimeter, a controllable heat input for supplying any additional energy necessary to superheat the steam sample, and logic for deriving the dryness from the collected data. The NCG meter includes a cooler for condensing the steam sample reservoirs into which the liquid and non-condensable gases are entrapped and measured, and logic for continuously deriving the NCG ratio from the collected data.

8 Claims, 7 Drawing Sheets

(56) References Cited

OTHER PUBLICATIONS

"overSteam 3" product information sheet, undated, available from Idoneus Anlagenbau GmbH.

Supplementary Partial European Search Report for corresponding European patent application No. EP 12843025.3, dated Jun. 22, 2015.

* cited by examiner

STEAM QUALITY MEASUREMENT SYSTEM

CROSS-REFERENCE TO RELATED APPLICATION

This application is the U.S. national phase of PCT Application No. PCT/US2012/053353 filed on Aug. 31, 2012, published as WO 2013/062673, which claims the benefit of U.S. Provisional Application No. 61/552,557 filed on Oct. 28, 2011, the disclosures of which are incorporated in their entirety by reference herein.

TECHNICAL FIELD

This invention relates to a system and method for measuring steam quality.

BACKGROUND

Steam is used as a source of power in a variety of applications, including steam generators and steam turbines. Steam is used for heating, sterilizing, humidifying, and evaporating in several sectors such as oil refining, nuclear power plants, and food plants, as well as pharmaceutical manufacturing plants. In certain applications it is critical to know the quality of the steam used, that is, the dryness and non-condensable gases content of the steam, since any deviation in steam quality for these critical applications would create undesirable consequences. Bad steam quality is not suitable for sterilizing, can erode turbine blades, and can create water hammer in piping.

Until now such measurements required human intervention for a manual sampling of the steam. This manual process is not fully reliable, is time consuming and is not safe (for example, risk of burning while installing the connections for the sampling, or while taking the samples).

Steam dryness may be determined in several ways, including by using a throttling calorimeter. Examples of known steam quality measurement systems and methods are disclosed in U.S. Pat. No. 4,833,688, issued to Smith, and U.S. Pat. No. 5,327,772, issued to Fredricks.

For the throttling calorimeter to provide useful steam quality data, the steam sample must be in a single phase (i.e., gaseous). This may be achieved by ensuring that the steam is in a superheated state. For the majority of industrial steam systems that have working pressures above 10 bar this is easily achieved by reducing the pressure. Unfortunately, this method has a limited working range for low pressure systems, for example, those operating at 3 bar gauge (e.g., 97% dryness). This method is therefore unsuitable for pharmaceutical industry steam applications that utilize steam at a relatively low pressure and require measurement of dryness across a range of 90 to 100%.

It is also desirable to measure and monitor the content of non-condensable gases (i.e., air) in the steam.

It is also desirable to measure whether the steam is in a "superheated" condition.

SUMMARY

The disclosed system and method continually and automatically measures the quality of steam flowing through a conduit by passing the steam through a steam dryness meter, then condensing the steam in a non-condensable gases (NCG) meter to provide real-time dryness and non-condensable gas volume measurements.

The disclosed system includes a steam dryness meter including a throttling calorimeter which has a calibrated orifice through which a steam sample enters from the steam system conduit, without working, into the inner chamber of the calorimeter at atmospheric pressure, a first sensor for sensing the pressure of the steam before it enters the calorimeter, a second sensor for sensing the temperature of the steam sample after the steam has entered the inner chamber of the calorimeter, a controllable and measurable heat input for supplying any additional energy necessary to superheat the steam sample, a third sensor for measuring the steam temperature after the heat input, and logic for deriving a dryness value from the collected data.

The disclosed system further comprises an NCG meter including an injector for injecting the steam sample as it exits the dryness measurement device into a cooler for condensing the superheated steam sample. The condensed sample then flows from the cooler/condenser coil into a reservoir under an inverted bucket (mounted in the reservoir) into which the non-condensable gases rise and are entrapped. A first differential pressure sensor is operably connected to the inverted bucket to sense the pressure of the entrapped air. When the differential pressure of the entrapped air is determined to have reached a predefined threshold, the volume of entrapped air (which has now accumulated to a known volume) is recorded and the accumulated gas volume evacuated from the inverted bucket. A second differential pressure sensor is operably connected to the reservoir to sense the pressure of the condensed steam in the reservoir. When the differential pressure of the condensed steam is determined to have reached a predefined threshold, the accumulated volume of condensate (which has now accumulated to a known volume) is recorded, and a controllable valve is activated to discharge the accumulated liquid from the reservoir. The system includes logic for deriving an NCG ratio from the collected data. In this manner, the volumes of the entrapped air and condensate are continuously monitored, and an NCG ratio repeatedly derived, as the condensed steam sample is continuously routed through the non-condensable gases meter from the steam system.

In one embodiment, the NCG meter utilizes two reservoirs which are interconnected by a three-way valve to collect the condensate. In this embodiment, the condensed sample flows from the cooler/condenser coil into a first reservoir under an inverted bucket (mounted in the reservoir) into which the non-condensable gases rise and are entrapped, and, as well, into a second reservoir, which is connected to the first reservoir via the (normally open) valve. As described above, the first differential pressure sensor is operably connected to the inverted bucket to sense the pressure of and evacuate the entrapped air when the air is determined to have reached the predefined threshold. The second differential pressure sensor is operably connected to the second reservoir to sense the pressure of the condensed steam in the reservoirs. When the differential pressure of the condensed steam is determined to have reached a predefined threshold, the three-way valve is activated to momentarily block the flow of the condensate from the first reservoir into the second reservoir and discharge the accumulated liquid from the second reservoir.

The disclosed system employs a computer operably connected to the sensors utilized in each of the steam dryness meter and the non-condensable gas meter, and programmed to include (1) first logic for determining the dryness of the steam sample based upon the sensed steam sample conditions, and (2) second logic for determining the ratio of condensed liquid to non-condensable gases (the NCG ratio) in the condensed steam sample.

The disclosed system may also include a monitor, printer, or other means of displaying the derived dryness and NCG ratio data, either on a periodic or continuous basis as desired, to allow the steam system operator to monitor the quality of the steam based upon steam quality data automatically developed in real-time by the system without the need for operator control.

BRIEF DESCRIPTION OF THE DRAWINGS

Embodiments of the present disclosure described herein are recited with particularity in the appended claims. However, other features will become more apparent, and the embodiments may be best understood by referring to the following detailed description in conjunction with the accompanying drawings, in which:

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
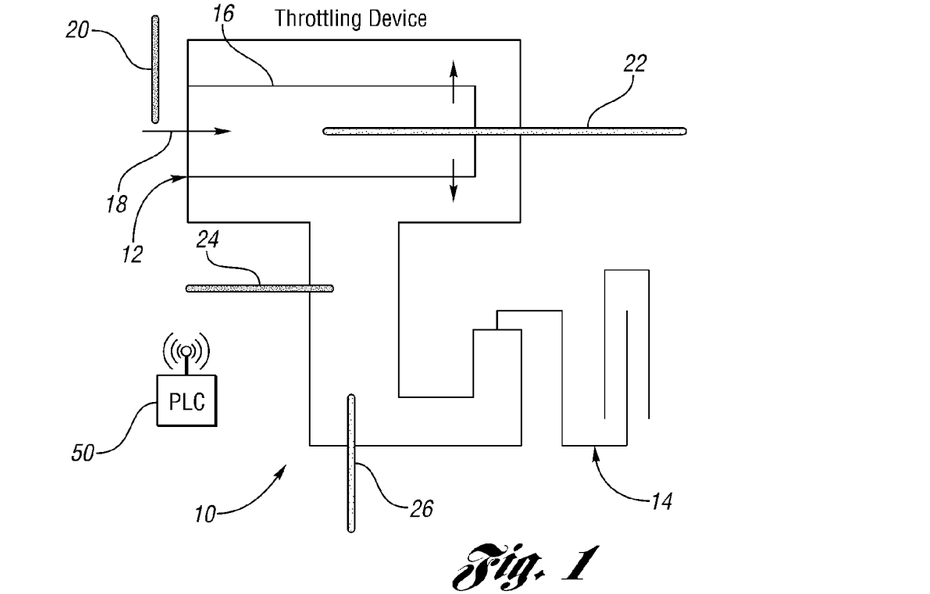
FIG. 1 is a schematic diagram of one embodiment of the disclosed system.

Referring to FIG. 1, the disclosed system 10 includes a steam dryness meter 12 and an NCG meter 14 each including various sensors, as described in detail hereinafter, for sensing certain conditions of a steam sample which has been diverted from the main steam line. The system 10 also includes a computer, such as, for example, a programmable logic controller (PLC), which is operably connected to the steam dryness meter sensors and the NCG meter sensors, and includes logic for calculating (1) the steam dryness of the sample based upon the sensed conditions, and (2) the non-condensable gases content of the sample based upon sensed conditions.

The steam dryness meter 12 includes a throttling calorimeter 16 which receives a diverted steam sample from the steam system through a calibrated orifice 18. A pressure sensor 20 is positioned upstream of the orifice 18 to provide data corresponding to the pressure of this steam before the steam enters the calorimeter 16. The orifice 18 is calibrated to provide an opening of sufficient size that the steam sample enters the inner chamber of the calorimeter 16 without doing work. A temperature sensor 22 is located within the calorimeter 16 to measure the temperature of the steam sample in the calorimeter. A heating unit 24, such as electrically controllable resistance heater is connected to provide a controlled, known amount of thermal energy to the steam sample in the calorimeter (in Area 3 shown in FIG. 1) to ensure that the steam sample is superheated, as confirmed by a second temperature sensor 26.

Referring again to FIG. 1, upon entering the calorimeter, the steam sample is at atmospheric pressure. The Joule-Thomson effect provides that the temperature of a gas will fall when it passes through an orifice without doing work. However, as the steam crosses the orifice 18, it does not lose any energy if it crosses the orifice without any work. Once the orifice 18 is crossed, the steam is at lower pressure (atmospheric pressure). The Mollier Diagram indicates that saturated steam at high pressure has more energy than saturated steam at lower pressure. Thus, while crossing the orifice, the steam, the excess energy will superheat the steam. Under this condition, the steam temperature and total enthalpy can be correlated.

Still referring to FIG. 1, using one method, since the initial pressure (prior to entering the calorimeter) and the current temperature of the steam are known, the system 10 can determined by reference to steam tables whether the current steam sample is superheated. If it is not in a superheated condition, the system 10 provides a measured amount of energy to heat the steam, via heater 24. Once the steam is heated sufficiently to place it in a single phase, superheated condition, the dryness of the steam sample can be derived from the initial pressure, the current temperature, and the measured quantity of heat input by the system.

Still referring to FIG. 1, in an alternative embodiment the disclosed system may employ another method for deriving the dryness of the steam. For a specific detected steam pressure in the pipe, it is possible to derive the hypothetical temperature of the steam at the orifice 18 if the steam had a dryness rating of 1. This can be done by reference to a Mollier diagram. As long as the sensor 22 shows a temperature lower than this hypothetical temperature then a measured amount of energy (heat) will be added via an electric resistance heater 24. Knowing the amount of energy that was added by the resistance heater allows the system to determine, by reverse calculation, the steam quality of the steam sample in the pipe.

Figure 2:
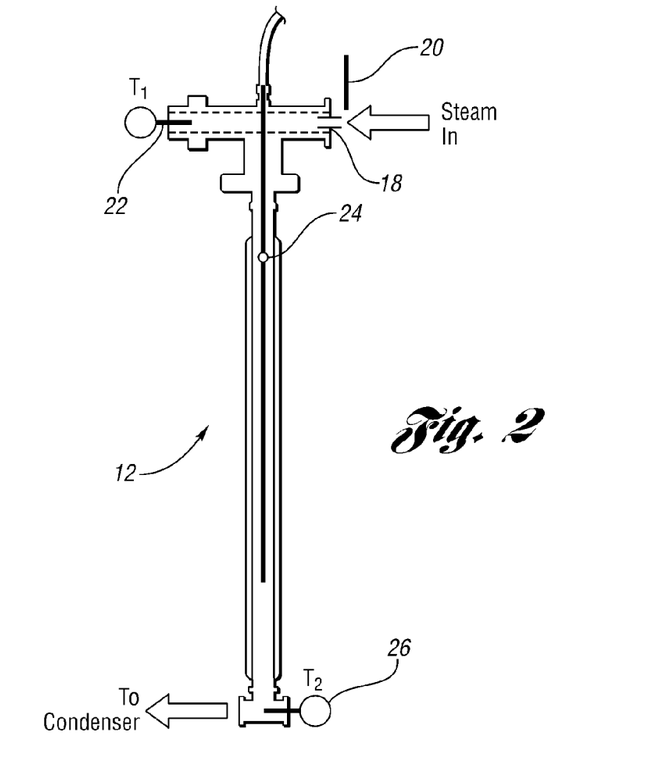
FIG. 2 is a partially schematic cross-sectional view of one embodiment of the throttling calorimeter dryness meter of the disclosed system.
Figure 3:
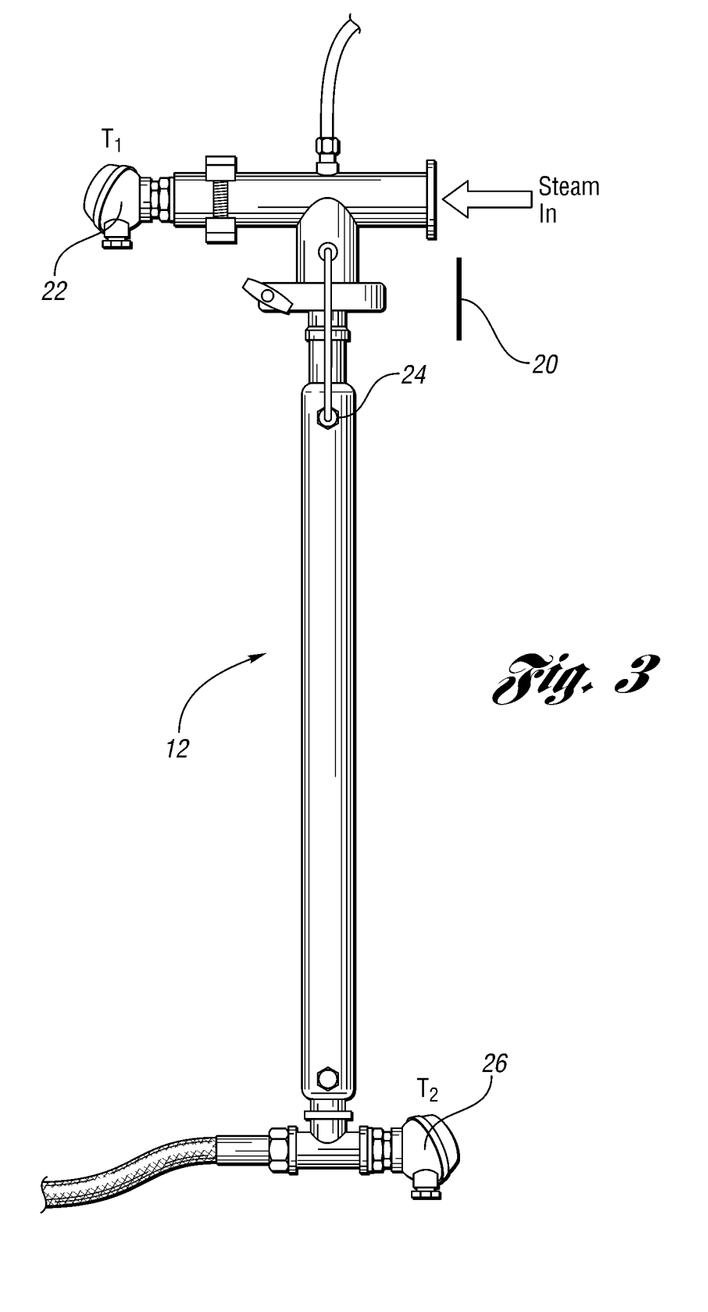
FIG. 3 is a perspective view of a throttling calorimeter used in one embodiment of the disclosed system.

FIGS. 2 and 3 illustrate one embodiment of the disclosed dryness meter 12 in, respectively, disassembled and assembled conditions. An electrical resistance heater would be mounted as shown in FIGS. 2 and 3 to serve as heater 24 in this embodiment.

Referring again to FIG. 1, as well as to FIGS. 4 and 5, one embodiment of the NCG meter 14 will now be described. The NCG meter 14 includes a cooler/condenser (cooler) 28 which receives the steam sample as it flows out of the throttling calorimeter 16, cools it and causes it to condense as it flows through coil 30 into a reservoir 32. An inverted bucket (shown as 34 in FIG. 4) is positioned within reservoir 32 over the opening in the coil 30 through which the condensed steam sample enters the reservoir such that any non-condensable gases (e.g., air) rise and are trapped within the inverted bucket 34. A differential pressure sensor 36 is operably connected to detect the differential pressure of the steam NCG in the inverted bucket 34. A solenoid valve 38 is operably connected to the outlet of the inverted bucket 34 so that, when the differential pressure of the accumulated NCG reaches a pre-determined threshold value (indicating that the accumulated volume of gases in the bucket have reached a pre-determined threshold), the system 10 records the accumulated gas volume and actuates the valve 38 to allow the accumulated NCG to be released from the inverted bucket 34.

Figure 4:
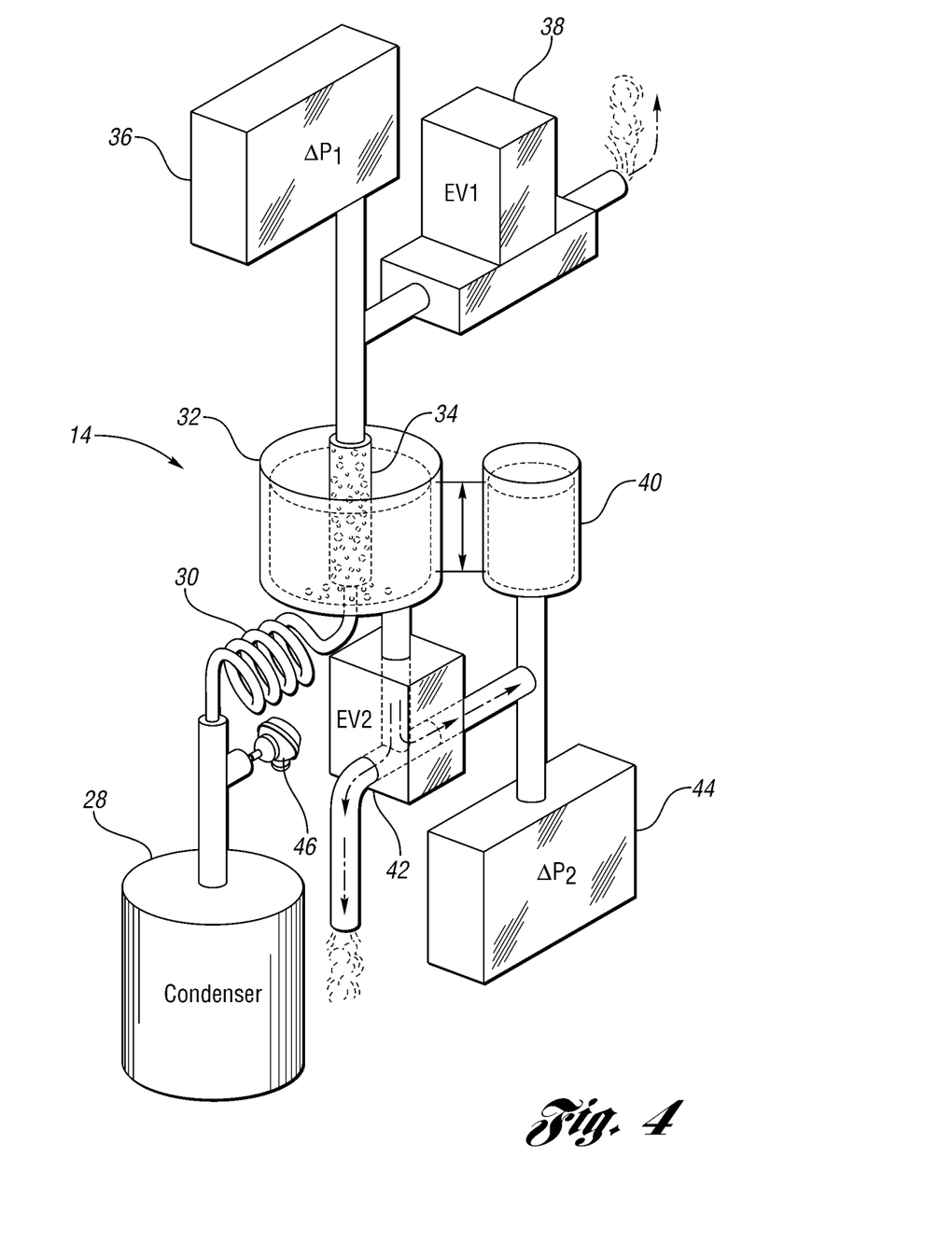
FIG. 4 is a schematic perspective view of one embodiment of the non-condensable gas meter of the disclosed system.
Figure 5:
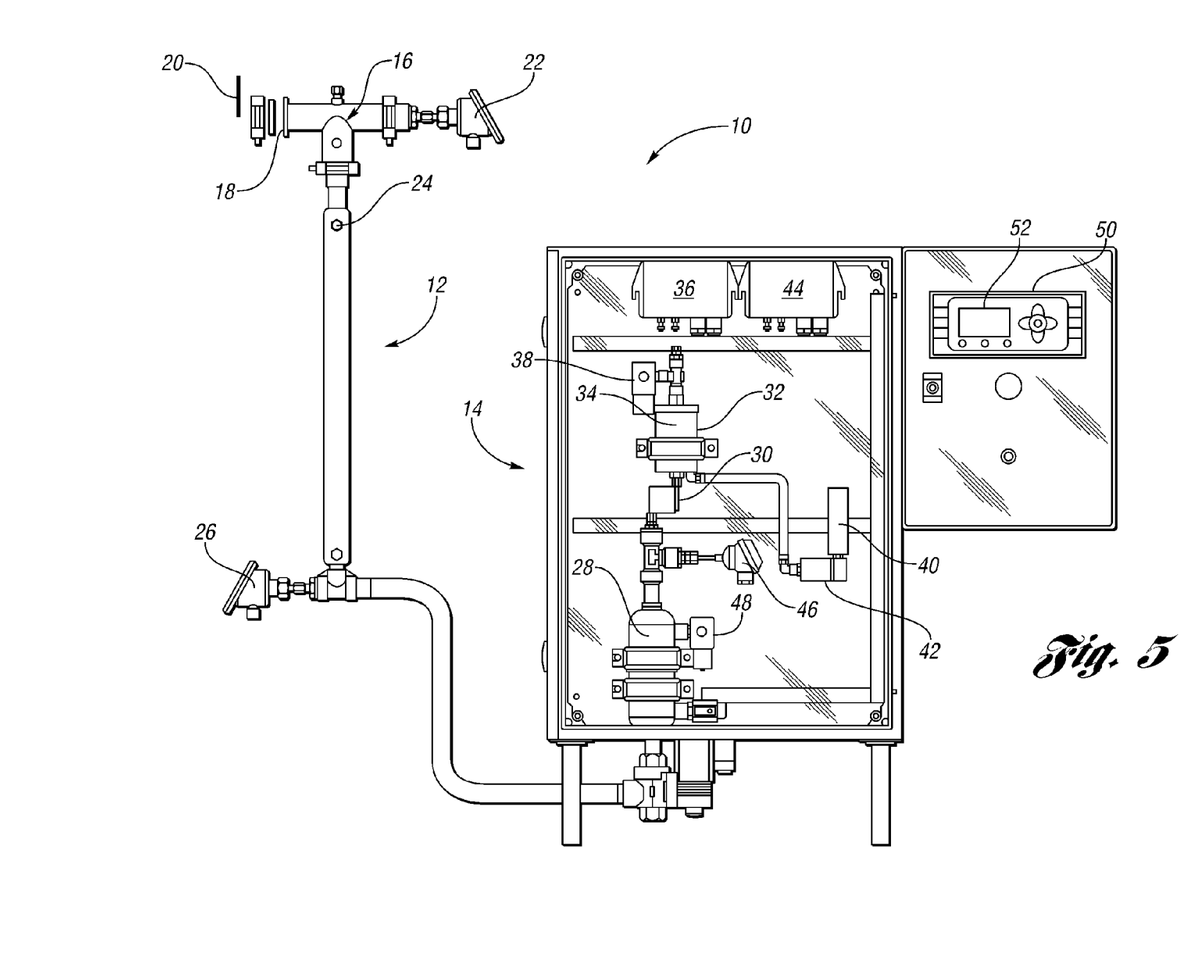
FIG. 5 is a perspective view of the disclosed system including one embodiment of the non-condensable gas meter of the disclosed system.

In the embodiment illustrated in FIGS. 4 and 5, condensate flows from the first reservoir 32 to the second reservoir 40 through a three-way valve 42. A second differential pressure sensor 44 is operably connected to detect the pressure of the accumulated condensed portion of the steam sample in reservoir 40. The three-way valve 42 is operably connected to the outlet of reservoir 32 (at the inlet of reservoir 40) and a discharge port (not shown). When the differential pressure of the accumulated condensed steam reaches a predetermined value (indicating that the accumulated volume of condensate in the reservoirs has reached a pre-determined threshold), the system 10 records the discharged condensate volume, and actuates the valve 42 to momentarily block the flow of condensate from the first reservoir 32 into the second reservoir and open the discharge port of the second reservoir 40 to allow the current volume of condensed steam to drain from the second reservoir 40. As will be explained in greater detail hereinafter, the system tracks the accumulated volumes of NCG and condensed steam for a selected time interval. At the lapse of each time interval the system then compares the accumulated volumes of non-condensable gas and condensed liquid steam to derive the ratio of the mass of the non-condensable gas and condensed liquid steam for the steam sample that flowed through the system for that interval. It will be appreciated that any suitable time interval may be adopted, depending upon the size of the reservoirs, the flow rate of the steam, and other system design and operation factors.

Referring to FIGS. 4 and 5, in this disclosed embodiment, the steam sample is condensed by injecting the sample in cooler 28 which cools the sample with the aid of cooling water (or, alternatively, another suitable coolant). The cooling water enters the cooler via an electro-mechanical (e.g., solenoid) valve 48 that is controlled based upon the measured temperature of the steam sample (via temperature sensor 46). Once condensed, the steam flows into and is entrapped in the inverted bucket as previously described.

As shown in FIG. 5, the disclosed system 10 employs a computer, in the form of a PLC 50, operably connected to (1) receive data from the sensors 20, 22, 26, 36, 44 and 46 utilized in each of the steam dryness meter and the non-condensable gas meter, and (2) operate the heater 24 and valves 38, 42, and 48. The PLC 50 is also programmed to include (1) first logic for determining the dryness of the steam sample based upon the sensed steam sample conditions, and (2) second logic for determining the ratio of condensed liquid to non-condensable gases (the NCG ratio) in the condensed steam sample. The PLC 50 is programmed to operate the heater 24, by activating the heater as required to controllably supply heat to the steam sample (shown at 3 in FIG. 1), as a function of the sensed pressure (from sensor 20) and temperature (from sensors 22 and 26. In one embodiment of the disclosed system, the control logic utilizes the sensed pressure and temperature and determines whether additional heat is required by reference to the steam tables stored in a lookup table in the computer's memory. In one particular embodiment, the system refers to a Mollier Diagram stored in the computer's memory.

The system illustrated in FIG. 5 also includes a monitor, or other suitable display device 52, suitably connected for displaying derived dryness/superheat information, and NCG ratio data on a continuous basis, to allow the steam system operator to monitor the quality of the steam based upon steam quality data automatically developed in real-time by the system without the need for operator control.

The PLC, temperature sensors, pressure sensors, valves and switches are commercially available from a variety of suppliers known to those of skill in the art. One suitable PLC is available from Yokogawa Corporation of America of Sugar Land, Tex.

In the illustrated embodiment of FIG. 5, the PLC is programmed to receive data from the sensed inputs, control the valves in the NCG meter, and derive the dryness and NCG ratios for the steam samples. It will be appreciated that the system may alternatively be designed such that the PLC performs less than all, or none, of the analysis of the sensed signals, but instead simply receives and transmits data corresponding to the sensed temperature and pressure and accumulated volume conditions to a central computer. Thus, the data analysis may be performed either by the PLC as shown in FIG. 5, by a central computer connected via a conventional network to one or more of the disclosed systems 10, or by each of the PLC and the central computer in some desired combination.

It should also be noted that, although the illustrated embodiment utilizes a single PLC to control the entire system 10, one or more programmable microprocessor(s), not shown, may be used in combination to implement the described system functions.

The methodology employed by the disclosed system 10 to develop and derive the steam dryness and NCG ratios are now further described with reference to FIGS. 6 and 7.

Figure 6:
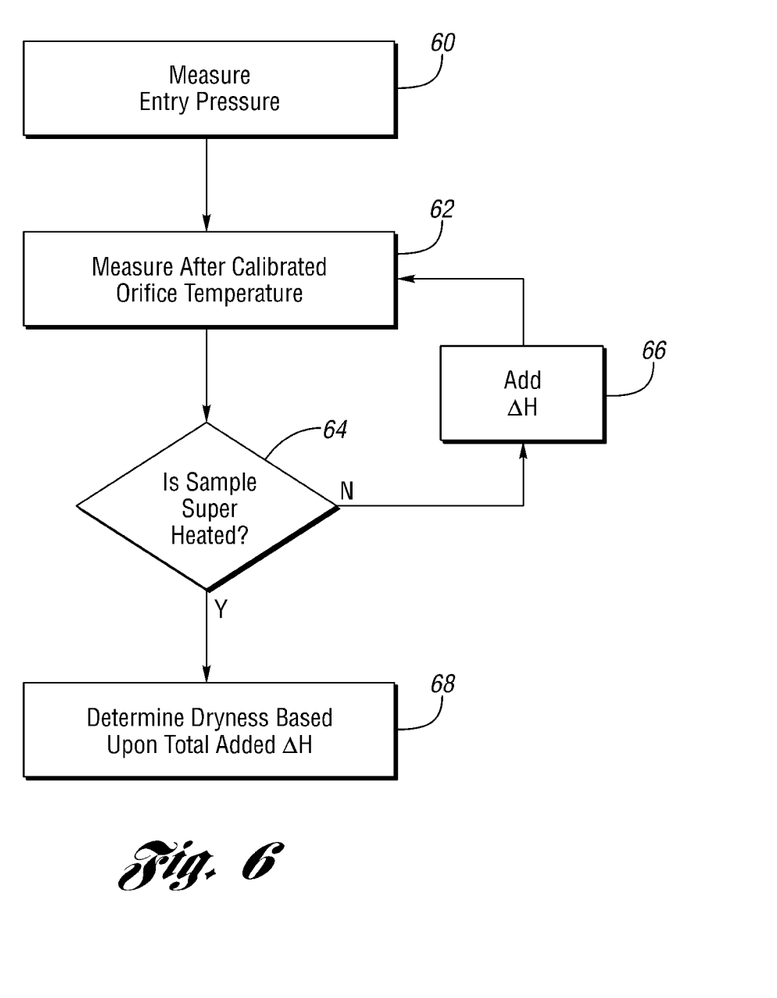
FIG. 6 is a flowchart depicting one disclosed method of deriving the dryness of the steam sample.

FIG. 6 illustrates one methodology used to determine the dryness of the steam. As previously described, and as indicated at 60, the system receives pressure data from sensor 20 indicative of the pressure of the steam sample prior to the steam entering the throttling calorimeter. The system, at 62, then measures the temperature of the steam at atmospheric pressure in the throttling calorimeter 16 after the steam enters through the calibrated orifice 18. Based upon these pressure and temperature values, the system, at 64, then determines whether the sample residing in the throttling calorimeter is in a superheated condition. If not, the system, at 66, activates the heater to supply a measured amount of thermal energy to the steam sample. The system then continually monitors the temperature of the steam to determine when the steam has reached a superheated state. Once the steam is reached a superheated state the system, at 68 then determines the dryness of the sample based upon the amount of energy input by the system to superheat the steam.

Figure 7:
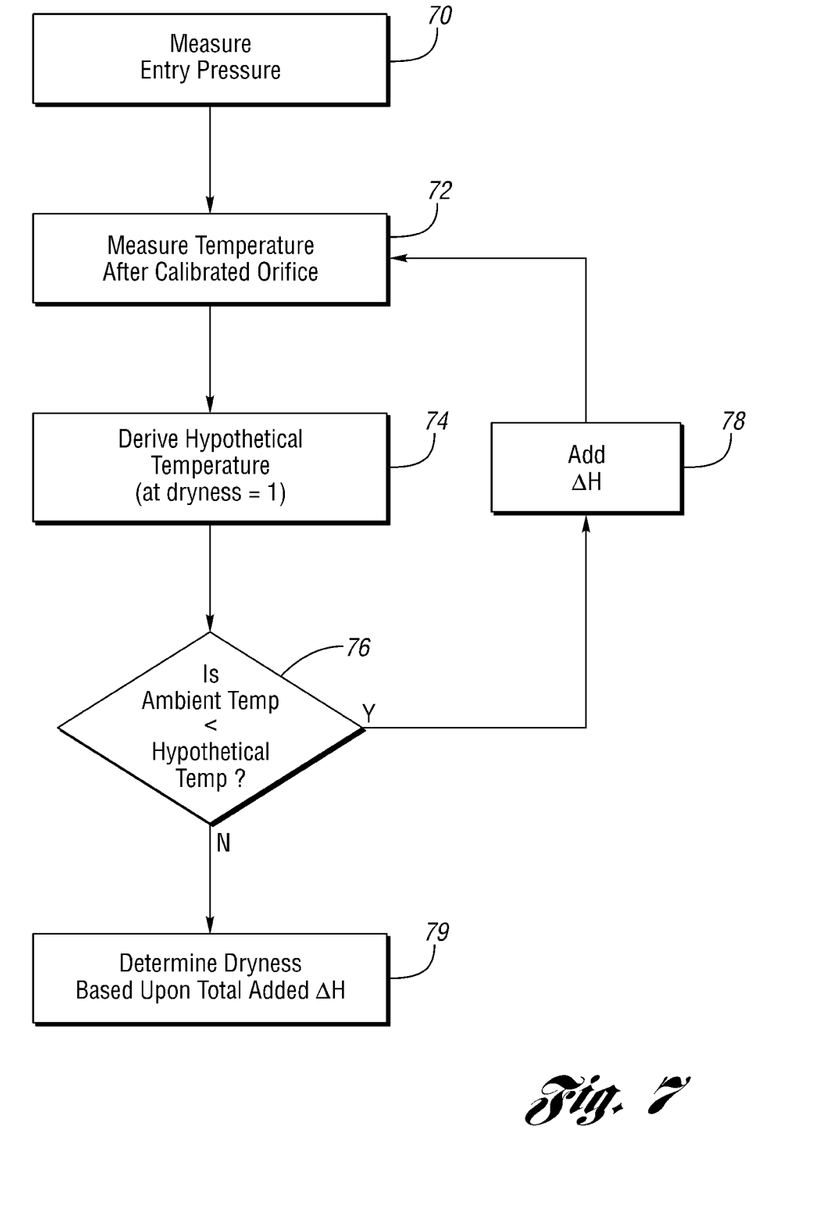
FIG. 7 is a flowchart depicting another disclosed method of deriving the dryness of the steam sample.

FIG. 7 illustrates another methodology used to determine the dryness of the steam. As previously described, and as indicated at 70, the system receives pressure data from sensor 20 indicative of the pressure of the steam sample prior to the steam entering the throttling calorimeter. The system, at 72, then measures the temperature of the steam (at atmospheric pressure) after is passes the calibrate orifice 18 in the throttling calorimeter 16. Based upon these pressure and temperature values, the system then determines whether the initial steam sample in the pipe has a dryness higher than 1. This can be done, as shown at 74, by extrapolating the temperature at the lower (atmospheric) pressure, based upon the known initial pressure and by using a Mollier Diagram stored in the PLC. If, at 76, it is determined that the temperature measured at 22 is lower than the extrapolated hypothetical temperature, then the system, at 78, activates the heating element to heat the sample. The system then continually monitors the temperature of the steam sample to determine when the steam has reached the extrapolated temperature. Once the steam has reached the extrapolated temperature, at 79, the system then determines the dryness of the sample based upon the amount of energy input by the system (i.e., the resistance element 24) to superheat the steam.

In the disclosed embodiments, the system 10 expresses steam dryness as a ratio of (the mass of dry steam) to (the mass of dry steam plus the mass of water). Thus, the dryness value, X, will have a value between 0 and 1, with X=0 corresponding to water, and X=1 corresponding to 100% dry steam. If X>1 then the initial steam in the pipe is superheated.

Figure 8:
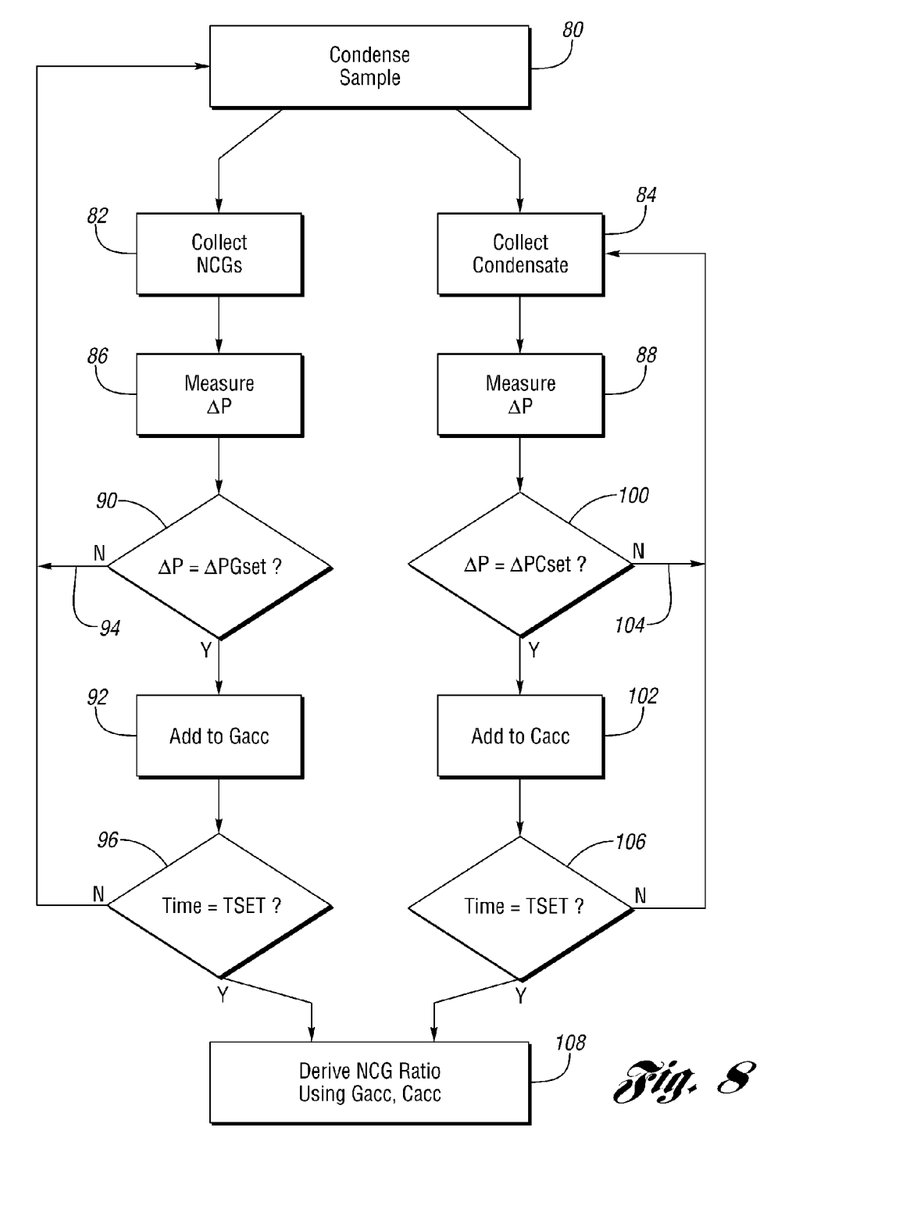
FIG. 8 is a flowchart depicting the disclosed method of deriving the non-condensable gases in the steam sample.

FIG. 8 illustrates the methodology employed by the disclosed system to derive the NCG content (which may be expressed as a ratio, X, of the masses of the non-condensable gases to the condensed liquids). As previously described the steam sample, upon exiting the dryness meter 16, enters the NCG meter 14 and the steam sample is condensed, as indicated at 80. Again, as previously described, the NCG is accumulated, at 82, and the liquid steam condensate is accumulated, at 84. The system then measures the differential pressures of the NCG and condensed steam, respectively at 86 and 88. The differential pressure of the non-condensable gas and the condensed liquid are compared, respectively at 90 and 100, to preset pressure values, $\Delta PG_{set}$, for the gas, and $\Delta PC_{set}$ for the condensate. These preset values represent known volumes of the gas and condensate.

If the differential pressure of the NCG has reached the preset value, $\Delta PG_{set}$, the system, at 92, activates a valve to release the entrapped gas and adds the known volume to the accumulated gas volume, $G_{acc}$. Similarly, if the differential pressure of the condensed liquid steam has reached the preset value, $\Delta PC_{set}$, the system, at 102, activates a valve to release the liquid in the reservoir and adds the known volume to the accumulated condensate volume, $C_{acc}$.

If the differential pressure of the NCG has not reached the preset value, the system, at 94, allows the gas to continue to collect within the inverted bucket. Similarly, if the differential pressure of the condensate has not reached its corresponding preset value, the system, at 104, allows the condensate to continue to fill the reservoirs.

The system 10 continues to collect and record the volumes of non-condensable gases and condensed liquid steam until a predetermined time interval lapses, at 96 and 106, at which time the system derives the respective masses and NCG ratio, at 108, using the recorded accumulated gases and condensed liquid data, $G_{acc}$ and $C_{acc}$. In the disclosed embodiment, the system expresses this ratio in $cm^3$ NCG/$cm^3$ of condensate.

It will be appreciated by those skilled in the art that there are various important controls that must be in place in the system to ensure that the dryness and non-condensable gas measurements are accurate. For example, the size of the calibrated orifice must be continuously monitored to determine whether an unacceptable level of erosion or blockage has occurred. Secondly the heat loss of the whole system must be calibrated. Third, all temperature and pressure probes must be calibrated.

One methodology that may be utilized to monitor the state of the calibrated orifice includes periodic determination of the time required to collect the condensate. If the time required to collect the condensate increases, but the steam pressure remains the same, the increase is an indication that the orifice has become blocked. Similarly, if the time taken to collect the condensate decreases, but the steam pressure remains the same, then the orifice has become eroded and requires recalibration.

It will thus be appreciated that the disclosed system measures steam quality (i.e., dryness/superheat) and non-condensable gases ratio to a high degree of accuracy. Moreover, the disclosed system can be continuously monitored remotely, and calibrated to ensure consistent accuracy with no human intervention at the collection of data, dryness calculations, or non-condensable gases content calculations, and minimal human intervention for calibration.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for measuring the quality of steam flowing through a conduit including
    a steam dryness meter having a throttling calorimeter, at least one sensor for sensing a thermodynamic condition of the steam upstream of the calorimeter, at least one other sensor for sensing the condition of the steam sample in the calorimeter, and a controllable heat input for applying heat to the steam sample;
    a non-condensable gases meter including, a cooler for condensing a superheated steam sample, and a reservoir including an inverted bucket where the condensate and non-condensable gases separate and are entrapped, at least one sensor operably connected to the inverted bucket, at least one other sensor operably connected to the reservoir; and
    a computer operably connected to the sensors in the steam dryness meter and the non-condensable gases meter for periodically receiving the data signals corresponding to the sensed steam sample conditions in each of the steam dryness meter and the non-condensable gases meter, the computer including first logic on a computer readable medium, which first logic may be executed by the computer for determining the dryness of the steam sample based upon the sensed steam sample conditions and second logic on a computer readable medium, which second logic may be executed by the computer for determining the ratio of water to non-condensable gases in the condensed steam sample based on the sensed steam sample conditions in the inverted bucket and the reservoir.

2. The system of claim 1 further including a display for displaying the derived dryness and NCG ratio data on a periodic basis.

3. The system of claim 1 wherein the dryness meter includes a pressure sensor for sensing the pressure of the steam upstream of the calorimeter, and a temperature sensor for sensing the temperature of the steam sample in the calorimeter.

4. The system of claim 1 the controllable heater in the dryness meter is an electric resistance heater.

5. The system of claim 1 wherein the sensor operably connected to the inverted bucket is a pressure sensor, and the sensor operably connected to the reservoir is another pressure sensor.

6. The system of claim 1 wherein the computer is a single programmable logic controller.

7. The system of claim 1 wherein the dryness meter includes a calibrated orifice through which the diverted steam sample enters from the conduit without working, the at least one sensor for sensing a thermodynamic condition of the steam upstream of the calorimeter is a pressure sensor, the at least one other sensor for sensing a condition of the steam sample in the calorimeter is a temperature sensor, and the controllable heater is an electric resistance heater.

8. A system for measuring the quality of steam flowing through a conduit includes (1) a diverter for diverting a sample of the steam from the conduit, (2) a steam dryness meter having, a throttling calorimeter including a calibrated orifice through which the diverted steam sample enters from the conduit without working, a pressure sensor for sensing the pressure of the steam upstream of the calorimeter, a first temperature sensor for sensing the temperature of the steam sample in the calorimeter, and a controllable heat input for heating the steam sample, (3) a non-condensable gas meter including a cooler for condensing the superheated steam sample, an injector for injecting the condensed steam into a reservoir including an inverted bucket where the condensed liquid and non-condensable gases are separated and entrapped, a first pressure sensor operably connected to the inverted bucket for measuring the pressure of the entrapped gases, a second pressure sensor operably connected to the reservoir for measuring the pressure of the entrapped condensate, (4) a computer operably connected to the pressure sensor and the temperature sensor in the steam dryness meter and the first pressure sensor and the second pressure sensor in the non-condensable gas meter for periodically receiving the data signals corresponding to the sensed steam sample conditions in the steam dryness meter and the collected condensed water and non-condensable gases in the non-condensable gas meter, the computer including first logic on a computer readable medium, which first logic may be executed by the computer for determining the dryness of the steam sample based upon the sensed steam sample conditions and second logic on a computer readable medium, which second logic may be executed by the computer for determining the ratio of condensate to non-condensable gases in the condensed steam sample, and (5) a display for displaying the derived dryness and NCG ratio data, either on a periodic or continuous basis, as desired.

* * * * *